(12) United States Patent
Graham

(10) Patent No.: US 7,722,353 B2
(45) Date of Patent: May 25, 2010

(54) ORTHODONTIC INTERPROXIMAL LOCKING PLIERS

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 446 days.

(21) Appl. No.: 11/372,399

(22) Filed: Mar. 10, 2006

(65) Prior Publication Data

US 2007/0212658 A1    Sep. 13, 2007

(51) Int. Cl.
*A61C 3/00* (2006.01)
(52) U.S. Cl. .................. 433/4; 433/159; 81/424.5; 606/207
(58) Field of Classification Search .......... 433/4, 433/3, 24, 18, 159, 160, 161, 162, 149, 156; 81/3.6, 418, 420, 424.5, 426, 426.5; 76/64, 76/69; D24/153; D19/72; 227/54, 144; 72/409.01; 30/363, 364; 29/21.1; 606/207; D8/52
See application file for complete search history.

(56) References Cited

U.S. PATENT DOCUMENTS

| | | | | |
|---|---|---|---|---|
| 340,896 | A * | 4/1886 | Starr | 433/156 |
| 356,729 | A * | 1/1887 | Reeve, Jr. | 29/232 |
| 388,619 | A * | 8/1888 | Booth | 433/39 |
| 404,811 | A * | 6/1889 | Wichelhaus | 86/40 |
| 673,193 | A * | 4/1901 | Callison et al | 227/55 |
| 684,984 | A * | 10/1901 | Graft | 433/156 |
| 753,936 | A * | 3/1904 | Tull et al | 30/363 |
| 770,162 | A * | 9/1904 | Chase | 433/156 |
| 796,120 | A * | 8/1905 | Green | 433/39 |
| RE14,065 | E * | 2/1916 | Fenstermacher | 72/404 |
| 1,176,793 | A * | 3/1916 | Tuttle | 29/21.1 |
| 1,670,361 | A | 5/1928 | Johnson | |
| 2,314,884 | A * | 3/1943 | Klein | 174/84 C |
| 2,806,394 | A | 9/1957 | Briegel | |
| 2,959,858 | A | 11/1960 | Drake | |
| 2,985,962 | A * | 5/1961 | Shiner | 433/4 |
| 3,069,686 | A * | 12/1962 | Smith | 72/409.01 |
| 3,557,792 | A * | 1/1971 | Rubin | 606/207 |
| 3,781,993 | A * | 1/1974 | Cusato | 433/4 |
| 3,805,792 | A * | 4/1974 | Cogley | 606/142 |
| 3,984,041 | A * | 10/1976 | LePage et al. | 227/76 |
| 4,023,450 | A * | 5/1977 | Ygfors | 81/418 |
| 5,147,365 | A * | 9/1992 | Whitlock et al. | 606/88 |
| 5,197,879 | A | 3/1993 | Fowler, III | |
| 5,291,772 | A * | 3/1994 | Ferraro | 72/476 |
| 5,542,947 | A * | 8/1996 | Treacy | 606/88 |
| 5,617,619 | A * | 4/1997 | Knudson | 29/21.1 |
| 5,993,210 | A * | 11/1999 | Godfrey | 433/159 |
| 6,293,790 | B1 | 9/2001 | Hilliard | |
| 6,560,838 | B1 * | 5/2003 | Ito et al. | 29/402.11 |
| 6,666,683 | B2 * | 12/2003 | Mungcal | 433/149 |
| 6,814,574 | B2 | 11/2004 | Abolfathi | |
| 2003/0083747 | A1 * | 5/2003 | Winterbottom et al. | 623/17.11 |
| 2005/0255421 | A1 * | 11/2005 | Michaelson | 433/4 |

FOREIGN PATENT DOCUMENTS

JP        2003300171 A  * 10/2003

* cited by examiner

*Primary Examiner*—Ralph A Lewis

(57) ABSTRACT

This invention pertains to pliers for increasing the interproximal retention of thermoplastic appliances by denting the appliances in the interproximal areas between the teeth, especially denting the thermoplastic material at the interproximal gingival area.

17 Claims, 3 Drawing Sheets

ORTHODONTIC INTERPROXIMAL LOCKING PLIERS

FIELD OF THE INVENTION

The present invention is directed to orthodontic pliers that enhance the retentive ability of thermoplastic appliances. The pliers indent the thermoplastic material in the interproximal area between adjacent teeth. The pliers tips are shaped to conform to the interproximal area between adjacent teeth extending from the contacts between the teeth to the gingival area. The indenting of the thermoplastic appliance is done while the appliance is out of the mouth or in the mouth while the patient is wearing the appliance.

BACKGROUND OF THE INVENTION

Removable orthodontic appliances are used to retain teeth in an aligned position and to move teeth. Retaining the orthodontic appliance on the teeth has long been a problem. Traditional Hawley type appliances use metal clasps for retention. These metal clasps are adjustable: although, retention has been difficult as evidenced by the variety of clasps, such as ball clasps and Adams clasps, developed to improve the retentive capabilities. The arrival of thermoformed appliances introduced an all plastic appliance without metal clasps for retention. Attempts, with limited success, have been made to add retentive clasps. The thermoforming process does not readily enclose wires. Wires are held in with acrylic which requires a thermoforming material which is compatible and will fuse with the acrylic. Some of the best thermoforming materials are not compatible with acrylic. Pliers have been developed to dent the plastic material in a variety of shapes. None of the devices have been successful in making the vacuum-formed appliances more retentive after the appliance has been constructed.

SUMMARY OF THE INVENTION

The present invention is directed to orthodontic pliers that enhance the retentive ability of thermoplastic appliances following the appliance construction. The forming tips of the pliers are shaped to fit the interproximal area between adjacent teeth. The interproximal area extends from the occlusal portion of the teeth to the gingival papilla. The interproximal area is approximately rectangular with the triangle apex at the occlusal portion of the teeth. In the third dimension, the triangle extends inwards at the gingival papilla area towards the axial centers of the teeth with the triangle apex towards the axial centers of the teeth. The three dimensional shape of the forming tip is; therefore, pyramidal. The inner part of the pyramid that faces the teeth forms a vertical ridge that follows the buccal or lingual embrasure inwards from the occlusal of the teeth as the embrasure opens towards the gingival. The extending of the pyramid inwards provides the retention when the appliance material is formed in this area by the pliers. Many appliances are used for retention immediately following the removal of a fixed orthodontic appliance. Often the interproximal gingival papilla is puffy and the resulting appliance fits poorly in this area. The present invention can be used to form this area either by pressing the material while the aligner is in the patient's mouth or by pressing the material outside the mouth.

In a preferred embodiment, the forming tips are pyramidal and mirror each other. In this embodiment the buccal and lingual embrasure areas may be formed simultaneously either while the patient is wearing the aligner or outside the mouth.

In another embodiment of the invention one tip of the pliers is the same pyramidal shape while the opposing tip is female shaped to receive the pyramidal tip. This embodiment is more similar to prior art and may only be used while the aligner is outside the mouth.

DETAILED DESCRIPTION OF THE INVENTION

The present invention is a pair of orthodontic pliers used for increasing the retention of thermoplastic appliances to a patient's teeth. Thermoplastic appliances are used as retainers to retain teeth following orthodontic treatment and also used as aligners to reposition misaligned teeth. Retention of the aligner thermoplastic appliance on the teeth is more of a problem. Tooth movement forces generated by the aligner to reposition teeth tend to dislodge the aligner from the patient's teeth making the aligner less effective in moving teeth. The orthodontic interproximal locking pliers are shaped to dent the retainers and aligners to more closely fit the interproximal gingival area of adjacent teeth. The result is an undercut which enhances the locking of the appliance on the patient's teeth. The tip areas of the pliers are shaped to closely match the buccal and lingual gingival interproximal area.

Figure 1:
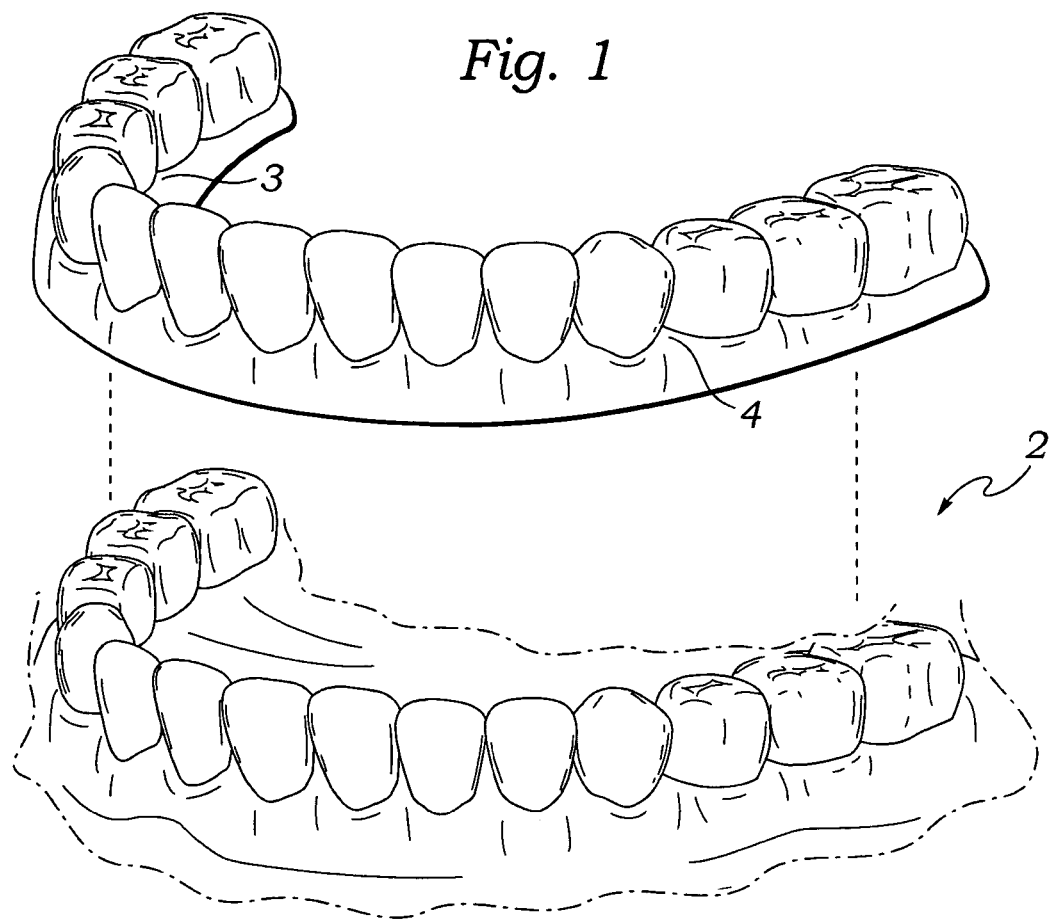
FIG. 1 is a perspective view of a thermoplastic appliance and teeth.
Figure 2A:
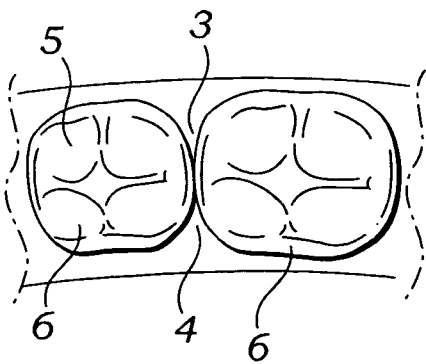
FIG. 2A is a top view of adjacent teeth.
Figure 2B:
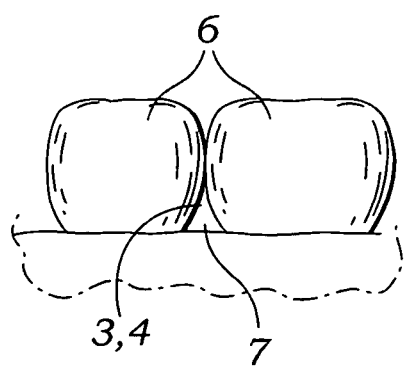
FIG. 2B is a side view of adjacent teeth.
Figure 3:
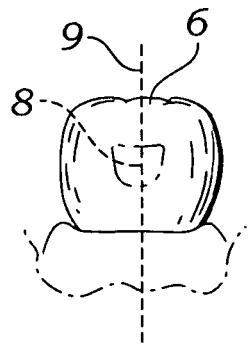
FIG. 3 is a side view of a tooth.
Figure 4:
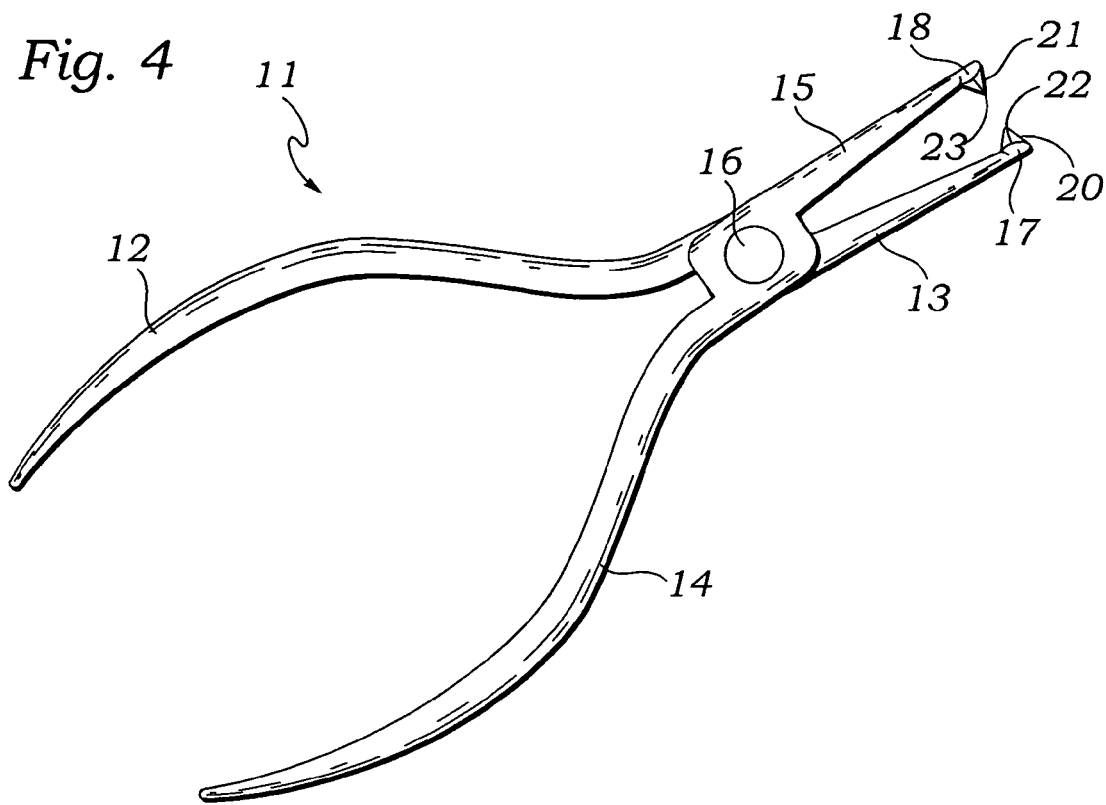
FIG. 4 is a top plan view of the orthodontic interproximal locking pliers.

FIG. 1 shows the thermoplastic appliance 1 as it fitted to a patient's teeth 2. The lingual interproximal area 3 and the buccal interproximal area 4 are to be dented. FIG. 2A shows an occlusal or top view 5 of two adjacent teeth 6 with the buccal embrasure 4 and lingual embrasure 5. FIG. 2B shows the gingival area 7 of the buccal 4 or lingual 3 embrasures of adjacent teeth 6. Buccal and lingual embrasures, 3 and 4, are formed between the adjacent teeth 6. Embrasures, 4 and 5, are formed where the adjacent teeth surfaces diverge from each other. The buccal 3 and lingual 4 embrasures extend from the occlusal 5 of the teeth 2 to the gingival 7. Note as the embrasure is followed to the gingival area 7 the embrasure area forms a triangle with its base at the gingival area. The embrasure is circling the interproximal contact area 8 between the teeth as shown in FIG. 3. As the buccal and lingual embrasures extend from occlusal to gingival another triangle is formed horizontally with its apex facing the teeth. This triangle extends from the buccal and lingual surfaces of the teeth inwards towards the axial center 9 of the teeth 6. This is the area the pliers tips 4, as shown in FIG. 4, are shaped to fit. The orthodontic interproximal locking pliers 11, as shown in FIG. 4, when used on the thermoplastic material in this area will produce a locking affect when the thermoplastic appliance 1 is placed upon a patient's teeth 2, as shown in FIG. 1.

Figure 5:
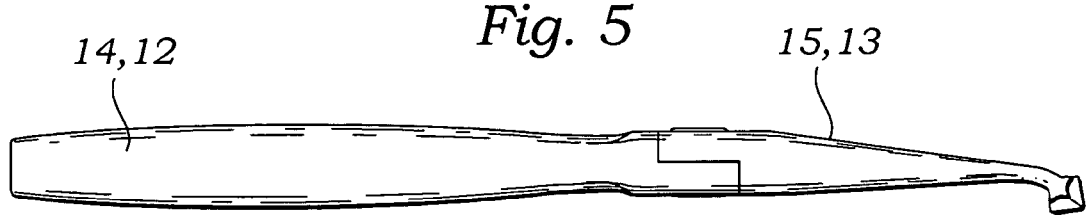
FIG. 5 is a side plan view of the orthodontic interproximal locking pliers.
Figure 6:
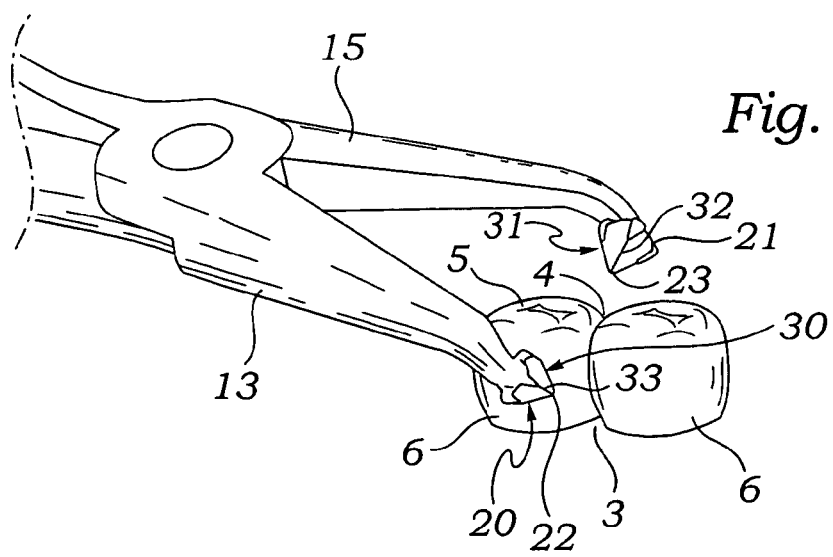
FIG. 6 is a perspective view of the orthodontic interproximal locking pliers and two adjacent teeth.
Figure 7:
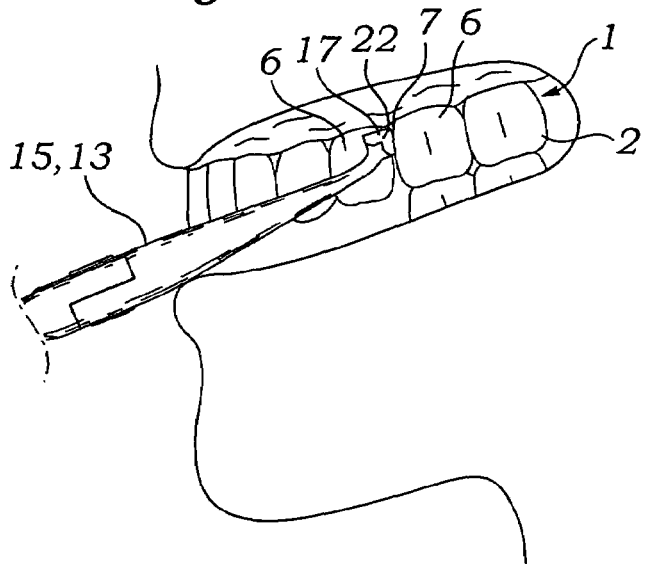
FIG. 7 is a perspective view of the orthodontic interproximal locking pliers and a thermoplastic appliance on the teeth.
Figure 8:
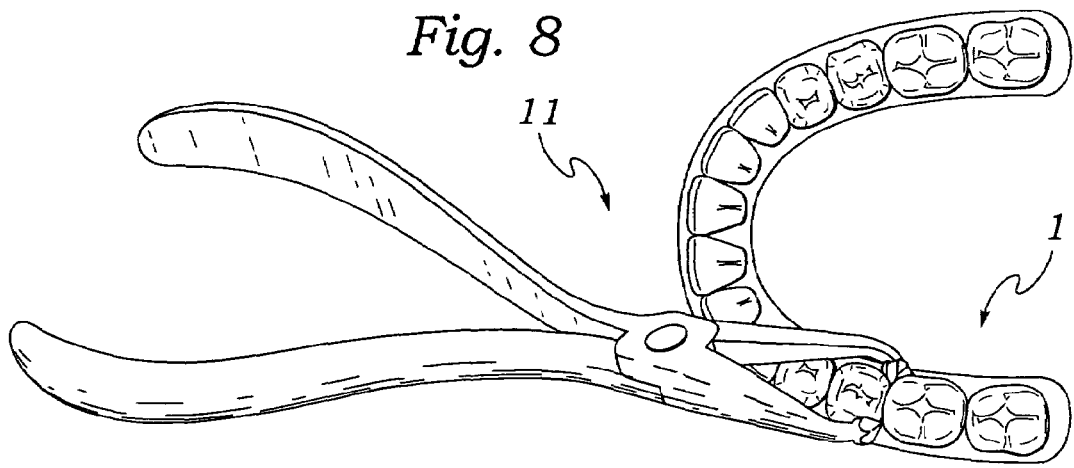
FIG. 8 is a perspective view of the orthodontic interproximal locking pliers and a thermoplastic appliance.

As shown in FIG. 4 the orthodontic interproximal crimping pliers 11 are comprised of a first handle 12 connected to a first jaw 13, a second handle 14 connected to a second jaw 15 and a pivot pin 5 joining the two jaw/handle combinations together pivotally. In a preferred embodiment in FIG. 4 the ends of the first jaw 13 and second jaw 15 define a first tip 17 and a second tip 18. The first tip 17 ends in a first pyramid 20, which is pyramidal in shape with a first pyramid apex 22 directed towards the second tip 18. The second tip 18 ends in a second pyramid 21 with a second pyramid apex 23 directed towards the first tip 17. As shown in FIG. 5 the first and second jaws, 13 and 15, curve downwards to ensure the body of the orthodontic interproximal crimping pliers 11 will not hit the teeth 2 when in use. As shown in FIG. 6 the base 31 of the second pyramid 21 and the base 30 of the first pyramid 20 face downwards or towards the gingival area 7, FIG. 2B, of the teeth 6. In FIG. 6, a second jaw 15 vertical ridge 32 extends vertically from the second ridge apex 23 of the second jaw 15. The vertical ridge 32 is fitted to the buccal embrasure 4 or lingual embrasure 3 of the adjacent teeth 6. A first jaw 15 vertical ridge 33 extends vertically from the first jaw apex 22 and is fitted to the buccal embrasure 4 or lingual embrasure 3 of the adjacent teeth 6. From the apex the inner edge of the pyramid curves upwards around the interproximal contact 8, as shown in FIG. 2. As shown in FIG. 6 the two apexes, 22 and 23, and vertical ridges, 32 and 33, fit the buccal and lingual embrasures, 3 and 4, simultaneously. In FIG. 7 the thermoplastic appliance 1 is placed on the teeth 2 and the first jaw 13 tip 17 is placed in the interproximal area between the adjacent teeth 6 with the first jaw apex 22 at the gingival area 7. The second jaw 15 tip 18 is placed on the opposite interproximal embrasure wherein the handles, 12 and 14, of the pliers 11 are squeezed adapting the interproximal thermoplastic material to the interproximal area of the adjacent teeth 6. This adapting procedure may be performed on the thermoplastic appliance 11 outside the mouth as shown in FIG. 8.

Figure 9:
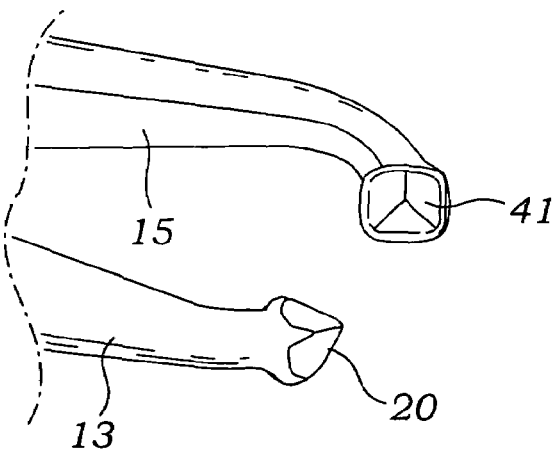
FIG. 9 is a prospective view of another embodiment of the orthodontic interproximal locking pliers.

In another embodiment shown in FIG. 9 only one jaw 13 contains the pyramid 20. The opposing jaw 15 contains a recess 41 shaped to receive the pyramid 20 of the opposing jaw 13 when the jaws are closed. This embodiment can only be used on the thermoplastic material 1 while it is outside the mouth.

In another embodiment of the invention the base apexes, 22 and 23, are a 1 mm ball.

The invention has been described with specific embodiments. However, the intent of the invention is to provide orthodontic interproximal crimping pliers that increase the retention of thermoplastic appliances on teeth. The orthodontic interproximal crimping pliers provide a locking of the thermoplastic material gingival to the contact points of adjacent teeth.

What is claimed is:

1. Orthodontic locking pliers for increasing the retention of an orthodontic thermoplastic appliance upon teeth comprising:
   a longitudinal first member having a first handle at one end and a first jaw with a first tip at the opposite end;
   a longitudinal second member having a second handle at one end and a second jaw with a second tip at the opposite end;
   a pivot pin connecting the first and second members pivotally wherein the first and second members cross so that the jaw portions are opposite each other and can be moved toward and away from each other into respective closed and open positions substantially along an imaginary plane by manipulating the handle about a longitudinal axis; and
   a single pyramidal projection on each of the first and second tips of the opposing first and second jaws, each pyramidal projection having three triangular sides comprised of a horizontal triangular base side and two connecting semi-vertical triangular sides wherein each triangular side shares a common apex facing the opposing jaw and each pyramidal projection having a semi-vertical ridge, formed by the junction of adjacent semi-vertical triangular sides, extending away from the horizontal triangular base side wherein the pyramidal projections are used to dent the thermoplastic appliance which contains vacuum-formed imprints of adjacent teeth with buccal and lingual interproximal embrasures extending from a gingival area to an occlusal area, the apexes of the pyramidal horizontal triangular bases sides are placed at the respective buccal and lingual interproximal gingival areas of the thermoplastic appliance and the semi-vertical ridges are placed in the buccal and lingual embrasures of the thermoplastic teeth wherein when closing the pliers the thermoplastic appliance is dented in a manner that retentive undercuts are formed in the buccal and lingual embrasure areas and the buccal and lingual interproximal gingival areas.

2. Orthodontic interproximal locking pliers as in claim 1 wherein the first and second jaws turn 45 degrees to the long axis of the pliers.

3. Orthodontic interproximal locking pliers as in claim 1 wherein the first and second jaws turn 90 degrees to the long axis of the pliers.

4. Orthodontic interproximal locking pliers as in claim 1 wherein the pliers are comprised of a metal alloy.

5. Orthodontic interproximal locking pliers as in claim 4 wherein the metal alloy is stainless steel.

6. Orthodontic interproximal locking pliers as in claim 1 wherein the pliers are comprised of plastic.

7. Orthodontic interproximal locking pliers as in claim 1 wherein the semi-vertical ridges have a semi-circular curve shaped to fit the interproximal contact point of adjacent teeth wherein the semi-circular shape enhances the adaptation of the thermoplastic material in the interproximal contact area when the thermoplastic material is dented with orthodontic interproximal locking pliers.

8. Orthodontic locking pliers for increasing the retention of an orthodontic thermoplastic appliance upon teeth comprising:
   a longitudinal first member having a first handle at one end and a first jaw with a first tip at the opposite end;
   a longitudinal second member having a second handle at one end and a second jaw with a second tip at the opposite end;
   a pivot pin connecting the first and second members pivotally wherein the first and second members cross so that the jaw portions are opposite each other and can be moved toward and away from each other into respective closed and open positions substantially along an imaginary plane by manipulating the handle about a longitudinal axis;
   a pyramidal projection at the tip of the first jaw having a top and a base with a base apex facing the second jaw, the pyramidal projection having three triangular sides comprised of a horizontal triangular base side and two connecting semi-vertical triangular sides wherein each triangular side shares a common apex and the semi-vertical triangles are joined fonning a semi-vertical ridge extending away from the horizontal triangular base side to the top of the pyramid from the base apex, the semi-vertical ridge has a semi-circular curve shaped to fit the interproximal contact point of adjacent teeth; and a pyramidal recess with three triangular sides at the tip of the second jaw facing the pyramidal projection of the first jaw, the pyramidal recess shaped to receive the pyramidal projection of the first jaw wherein the pyramidal projection and pyramidal recess are used to dent the thermoplastic appliance which contains vacuum-formed imprints of adjacent teeth with buccal and lingual interproximal embrasures extending from a gingival area to an occlusal area, the apex of the pyramidal horizontal triangular base is placed at the buccal or lingual interproximal gingival areas of the thermoplastic appliance and the semi-vertical jidge is placed in the buccal or lingual embrasure of the thermoplastic teeth wherein when closing the pliers the thermoplastic appliance is dented in a manner that retentive undercuts are formed in the buccal or lingual embrasure areas and the buccal or lingual interproximal gingival areas.

9. Orthodontic interproximal locking pliers as in claim 8 wherein the first and second jaws turn 45 degrees to the long axis of the pliers.

10. Orthodontic interproximal locking pliers as in claim 8 wherein the first and second jaws turn 90 degrees to the long axis of the pliers.

11. Orthodontic interproximal locking pliers as in claim 8 wherein the pliers are comprised of a metal alloy.

12. Orthodontic interproximal locking pliers as in claim 8 wherein the metal alloy is stainless steel.

13. Orthodontic interproximal locking pliers as in claim 8 wherein the pliers are comprised of plastic.

14. A method of increasing the retention of an orthodontic thermoplastic appliance with interproximal locking pliers wherein the locking pliers have opposing first and second tips, each tip with a pyramidal projection, the method of use comprising:

opening the jaws of the orthodontic interproximal crimping pliers;

placing the open pliers jaws pyramidal tips over the thermoplastic material in the buccal and lingual interproximal areas; and squeezing the handles of the pliers until the jaw projections dent the thermoplastic appliance.

15. A method of increasing the retention of an orthodontic thermoplastic appliance with interproximal locking pliers as in claim 14 wherein the thermoplastic appliance is adjusted by placing the thermoplastic on the teeth prior to simultaneously denting the adjacent buccal and lingual interproximal areas of the thermoplastic appliance with the pliers.

16. A method of increasing the retention of an orthodontic thermoplastic appliance with interproximal locking pliers, as in claim 14 wherein the thermoplastic appliance is adjusted by removing the thermoplastics appliance from the teeth prior to simultaneously denting the adjacent buccal and lingual interproximal areas of the thermoplastic appliance with the pliers.

17. A method of increasing the retention of an orthodontic thermoplastic appliance with interproximal locking pliers as in claim 14 wherein the locking pliers have opposing first and second tips, the first tip with. a three-sided pyramid and the second tip with a three-sided pyramidal recess, the method comprises the adjustment of the thermoplastic appliance by denting the buccal interproximal or lingual interproximal side of the thermoplastic appliance separately.

* * * * *